United States Patent
Ikeda et al.

(10) Patent No.: US 10,987,372 B2
(45) Date of Patent: Apr. 27, 2021

(54) ANTI-HEPATOMA-VIRUS AGENT

(71) Applicants: KAGOSHIMA UNIVERSITY, Kagoshima (JP); NATIONAL UNIVERSITY CORPORATION OKAYAMA UNIVERSITY, Okayama (JP); DAIKIN INDUSTRIES, LTD., Osaka (JP)

(72) Inventors: Masanori Ikeda, Kagoshima (JP); Midori Takeda, Kagoshima (JP); Masanori Baba, Kagoshima (JP); Nobuyuki Kato, Okayama (JP)

(73) Assignees: KAGOSHIMA UNIVERSITY, Kagoshima (JP); NATIONAL UNIVERSITY CORPORATION OKAYAMA UNIVERSITY, Okayama (JP); DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 16/083,762

(22) PCT Filed: Mar. 10, 2017

(86) PCT No.: PCT/JP2017/009674
§ 371 (c)(1),
(2) Date: Sep. 10, 2018

(87) PCT Pub. No.: WO2017/155082
PCT Pub. Date: Sep. 14, 2017

(65) Prior Publication Data
US 2019/0070207 A1 Mar. 7, 2019

(30) Foreign Application Priority Data

Mar. 11, 2016 (JP) .............................. JP2016-048664

(51) Int. Cl.
*A61K 31/7076* (2006.01)
*A61P 1/16* (2006.01)
*A61P 31/20* (2006.01)
*A61P 31/14* (2006.01)
*A61P 35/00* (2006.01)

(52) U.S. Cl.
CPC ............ *A61K 31/7076* (2013.01); *A61P 1/16* (2018.01); *A61P 31/14* (2018.01); *A61P 31/20* (2018.01); *A61P 35/00* (2018.01)

(58) Field of Classification Search
None
See application file for complete search history.

(56) References Cited

U.S. PATENT DOCUMENTS

| | | |
|---|---|---|
| 2005/0049220 A1 | 3/2005 | Stuyver |
| 2010/0009970 A1 | 1/2010 | Johansen et al. |
| 2013/0210757 A1* | 8/2013 | Chang ................ C07F 9/65586 514/47 |

FOREIGN PATENT DOCUMENTS

| | | | |
|---|---|---|---|
| CN | 101686673 A | 3/2010 | |
| CN | 104640444 A | 5/2015 | |
| JP | 2004-513083 | 4/2004 | |
| JP | 2004-534769 | 11/2004 | |
| JP | 2013-510904 | 3/2013 | |
| WO | 2002/018404 | 3/2002 | |
| WO | 2002/094289 A1 | 11/2002 | |
| WO | WO-2004035043 A1 * | 4/2004 | ........... A61K 31/282 |
| WO | 2008/033466 A2 | 3/2008 | |
| WO | 2008/128170 A1 | 10/2008 | |
| WO | 2011/060408 A2 | 5/2011 | |
| WO | 2013/187978 A1 | 12/2013 | |
| WO | 2015/013352 A2 | 1/2015 | |
| WO | WO-2015013352 A2 * | 1/2015 | ........... A61K 31/704 |

OTHER PUBLICATIONS

"Prevention" in Glossary of medical education terms: Parts 1-7. Wojtczak, A., Ed. Medical Teacher. vol. 24, Nos. 2-6 and vol. 25, No. 1&2. 2002. (Year: 2002).*
Midori Takeda et al., "Clofarabine exhibits multifunctional antiviral activity for hepatoma virus", Annual Meeting of the Molecular Biology Society of Japan Program, Nov. 30, 2016 (Nov. 30, 2016), Dai 39 Kai, p. 366, 3P-0669.
Takeda Midori, et al., "Clofarabine is a multifunctional direct acting antiviral (mDAA) for HBV and HCV", The Japanese Society of Virology Gakujutsu Shukai Program Shoroku-shu, Sep. 30, 2016 (Sep. 30, 2016), vol. 64, p. 198.
Chinese Intellectual Property Office, "Office Action with Search Report", issued in connection with corresponding Chinese patent application No. 201780015782.8 and dated Dec. 3, 2019 (6 pages).
Takahashi, Takeshi; et al., "Antitumor activity of 2-chloro-9-(2-deoxy-2-fluoro-beta-D-arabinofuranosyl) adenine, a novel deoxyadenosine analog, against human colon tumor xenografts by oral administration", Cancer Chemotherapy and Pharmacology, vol. 43, No. 3, 1999, pp. 233-240.

(Continued)

*Primary Examiner* — Dale R Miller
(74) *Attorney, Agent, or Firm* — Lucas & Mercanti, LLP

(57) ABSTRACT

It is an object of the present invention to provide a novel therapeutic agent for hepatoma viruses. Specifically, the present invention relates to an anti-hepatoma virus agent, containing as an active ingredient a compound represented by the following Formula (I) or a pharmaceutically acceptable salt thereof:

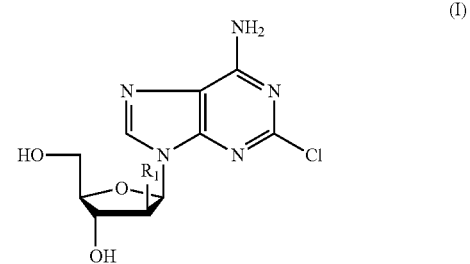

(wherein $R_1$ is fluorine or hydrogen).

10 Claims, 8 Drawing Sheets

Specification includes a Sequence Listing.

(56) References Cited

OTHER PUBLICATIONS

Bryant, Martin L.; et al., "Antiviral L-nucleosides specific for hepatitis B virus infection", Antimicrobial Agents and Chemotherapy, vol. 45, No. 1, 2001, pp. 229-235.
European Patent Office, "Supplementary European Search Report" issued in connection with EP patent application No. 17763422.7, dated Sep. 30, 2019 (5 pages).
European Patent Office, "Communication pursuant to Article 94(3) EPC" issued in connection with EP patent application No. 17763422.7, dated Oct. 11, 2019 (6 pages).

* cited by examiner

SEQUENCE LISTING

<160> NUMBER OF SEQ ID NOS: 2

<210> SEQ ID NO 1
<211> LENGTH: 18
<212> TYPE: DNA
<213> ORGANISM: Artificial
<220> FEATURE:
<223> OTHER INFORMATION: primer

<400> SEQUENCE: 1
gctcgtgtta caggcggg                                                  18

<210> SEQ ID NO 2
<211> LENGTH: 26
<212> TYPE: DNA
<213> ORGANISM: Artificial
<220> FEATURE:
<223> OTHER INFORMATION: primer

<400> SEQUENCE: 2
gaaccactga acaaatggca ctagta                                         26

ANTI-HEPATOMA-VIRUS AGENT

CROSS-REFERENCE TO RELATED APPLICATIONS

This application is a 371 of PCT/JP2017/009674, filed Mar. 10, 2017, which claims benefit of Japanese Patent Application No. 2016-048664 filed on Mar. 11, 2016.

TECHNICAL FIELD

The present invention relates to a novel therapeutic agent against, for example, hepatoma viruses.

BACKGROUND ART

Since Jenner discovered vaccine treatment against smallpox, infection prevention against viral infections has become available. However, regarding viruses for which there are no vaccines, once viral infection occurs, treatment options are limited to elimination of viruses by individual immunity and symptomatic treatment. The history of the development of antiviral agents against viruses begins with acyclovir that is a therapeutic agent for the herpes simplex virus developed by Elion et al. in 1977. In 1985, azidothymidine, which is a therapeutic agent for human immunodeficiency virus 1 (HIV-1), was discovered by Mitsuya et al. were found. There has been progress in the development of antiviral agents for some viruses such as HIV-1, hepatitis B virus (HBV), hepatitis C virus (HCV), and influenza viruses. However, antiviral agents do not exist for most of viruses at present.

HCV and HBV are hepatoma viruses that cause chronic hepatitis, liver cirrhosis, and liver cancer. It is estimated that there are about 2 million HCV-infected individuals in Japan and about 200 million HCV-infected individuals in the world. It is estimated that there are about 1.5 million HBV-infected individuals in Japan and about 3.5 billion HBV-infected individuals in the world. The number of HCV- and HBV-infected individuals accounts for about 8% of the world population, and therefore, HCV/HBV infection is one of the most important infections that must be overcome.

HCV is a virus belonging to the genus Hepacivirus of the family Flaviviridae and its genome is single-stranded plus RNA. The viral genome consists of about 9600 nucleotides, and all steps of viral replication and proliferation are carried out in the cytoplasm. Once the virus invades cells, first, a precursor protein consisting of about 3000 amino acid residues is produced. Next, 10 types of mature viral proteins are produced by the protease of the host and the protease of the virus. Among the 10 types of proteins, E1, E2, Core, and p7 are structural proteins necessary for viral particle production. NS2, NS3, NS4A, NS4B, NS5A, and NS5B are non-structural proteins necessary for viral replication. FIG. 1 illustrates the life cycle of HCV.

The life cycle of HCV is described as follows:
1) Infection
In a step of infection, the virus comes into contact with a receptor thereof so as to invade cells. At present, CD81, SR-B 1, Claudin1, Occludin, and the like are known as HCV receptors.
2) Translation
Most of host proteins require a Cap structure present at the 5' end of mRNA upon translation. On the other hand, HCV does not require such Cap structure. A ribosome is directly bound to a secondary structure of a region called "internal ribosomal entry site (IRES)" present on the 5' side of HCV, and then, a viral precursor protein (about 3000 amino acids) is translated by Cap-independent translation. Ten types of viral proteins are produced from the precursor protein by the protease of the host and the protease of the virus itself (NS3-4A).
3) Replication
Replication of HCV is performed by the replication complex formed with non-structural proteins. First, RNA-dependent RNA polymerase (NS5B) functions to synthesize negative-strand RNA that is a replication intermediate using the positive strand of the virus as a template. Next, NS5B replicates the viral genome of the plus-strand RNA using the minus-strand RNA as a template.
4) Particle Formation
Viral particle formation is completed as a result of the assembly of Core, E1, and E2 serving as structural proteins and the viral genome with a scaffold comprising endoplasmic reticulum and lipid droplets. It is known that NS5A plays an important role during particle formation.
5) Release
The viral particles are released extracellularly. It has been found that apolipoprotein is necessary upon release.

Proliferation of HCV described above occurs only in the cytoplasm.

Clinically applied direct-acting antivirals (DAAs), which can directly act on viruses, are targeted to NS3-4A that is a viral protease, NS5A necessary for viral replication and particle formation, and NS5B which is an RNA-dependent RNA polymerase. In the case of chronic hepatitis C, interferon (IFN) monotherapy was performed at first, however, efficacy was about 10% in this case. In 2015, a therapy involving the combination use of an NS5B inhibitor and an NS5A inhibitor was approved, for which efficacy at a level of 90% or more has been reported.

Meanwhile, FIG. 2 illustrates the life cycle of HBV. HBV is an incomplete double-stranded DNA virus belonging to the genus Orthohepadnavirus of the family Hepadnaviridae. Once HBV invades cells, it forms complete double-stranded DNA in the nucleus, which results in cccDNA. 3.6-, 2.4-, 2.1-, and 0.7-kb mRNAs are transcribed using DNA as a template and translated into a polymerase, HBcAg (Core), HBsAg, and an X protein, respectively. 3.6-kb pregenomic RNA (pgRNA) is packaged together with Core and the polymerase. After pgRNA is reverse-transcribed into DNA, viral particles are released extracellularly. Although HBV is not a retrovirus, as it has reverse transcription activity to polymerase, a reverse transcriptase inhibitor against HIV-1 is used for treatment of HBV.

In addition, for example, Patent Literature 1 discloses the use of 2'-fluoro-6'-methylene carbocyclic nucleosides for treatment of HBV and HCV infections. Patent Literature 1, however, discloses only the anti-HBV test as an antiviral test that was actually performed while failing to disclose that both HBV and HCV infections could be treated using 2'-fluoro-6'-methylene carbocyclic nucleosides.

CITATION LIST

Patent Literature

Patent Literature 1: JP Patent Publication (Kohyo) No. 2013-510904 A

SUMMARY OF INVENTION

Technical Problem

Most of refractory viral infections tend to be prolonged. There are the following problems related to HIV-1, HBV, and HCV for which there has been progress in the development of drugs as compared with other viruses: 1) acquisition of drug resistance through viral mutations; 2) very expensive drug prices; and 3) time-consuming drug development.

IFN is a physiologically active substance derived from a host and is able to eliminate a variety of viruses. Meanwhile, DAAs act only on particular viruses or are targeted to viruses of a group having similar viral enzymes (e.g. reverse transcriptases). As examples of the former, different antiviral agents are used for HBV that is a DNA virus and HCV that is an RNA virus because their life cycles are different. As examples of the latter, although HBV and HIV-1 are different in that they are a DNA virus and an RNA virus, since each of the two viruses has a reverse transcriptase that synthesizes DNA from RHA, an identical reverse transcriptase inhibitor may be effective for both viruses in some cases.

As described above, virus-specific agents are used as DAAs for viruses other than a group of viruses having the common enzyme. Therefore, it has been commonly known in the prior art that such agents do not act beyond the boundary between DNA viruses and RNA viruses which have different life cycles.

Therefore, the present invention is intended to develop a multifunctional DAA (mDAA) beyond the boundary between viruses having different life cycles. Assuming that the conventional DAA that cannot overcome the boundary between the life cycles is the first generation, mDAA having multifunctional antiviral activity as disclosed herein can be designated as an antiviral agent of the second generation.

In consideration of the above circumstances, it is an object of the present invention to provide an antiviral agent targeted to HBV and HCV that are hepatoma viruses causing liver carcinogenesis among five types of hepatitis viruses (A, B, C, D, and E) so as to prevent liver carcinogenesis.

Solution to Problem

As a result of intensive studies to achieve the above object, clofarabine has been found as an agent capable of suppressing proliferation of both HBV and HCV by conducting screening tests of HBV and HCV that are causative viruses of liver carcinogenesis in parallel in the present invention, although screening of one type of virus is usually conducted for screening of an antiviral agent. In addition, cladribine has been found as an agent capable of suppressing proliferation of HCV. This has led to the completion of the present invention.

Specifically, the present invention encompasses the following.
(1) An anti-hepatoma virus agent, which contains as an active ingredient a compound represented by the following Formula (I) or a pharmaceutically acceptable salt thereof:

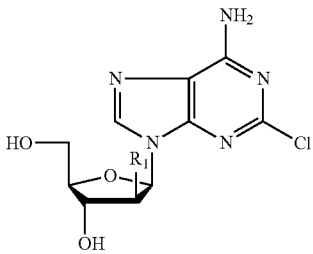

(I)

(wherein $R_1$ is fluorine or hydrogen).

(2) The anti-hepatoma virus agent according to (1), wherein the compound represented by Formula (I) or a pharmaceutically acceptable salt thereof is 2-chloro-9-(2-deoxy-2-fluoro-β-D-arabinofuranosyl)adenine (corresponding to "clofarabine") or a pharmaceutically acceptable salt thereof, and a hepatoma virus is HBV and/or HCV.
(3) The anti-hepatoma virus agent according to (1), wherein the compound represented by Formula (I) or a pharmaceutically acceptable salt thereof is 2-chloro-9-(2-deoxy-2-fluoro-β-D-arabinofuranosyl)adenine or a pharmaceutically acceptable salt thereof, and a hepatoma virus is HBV or HCV.
(4) The anti-hepatoma virus agent according to (1), wherein the compound represented by Formula (I) or a pharmaceutically acceptable salt thereof is 2-chloro-9-(2-deoxy-2-fluoro-β-D-arabinofuranosyl)adenine or a pharmaceutically acceptable salt thereof, and a hepatoma virus is HBV.
(5) The anti-hepatoma virus agent according to (1), wherein the compound represented by Formula (I) or a pharmaceutically acceptable salt thereof is 2-chloro-9-(2-deoxy-2-fluoro-β-D-arabinofuranosyl)adenine or a pharmaceutically acceptable salt thereof, and a hepatoma virus is HCV.
(6) The anti-hepatoma virus agent according to (1), wherein the compound represented by Formula (I) or a pharmaceutically acceptable salt thereof is 2-chloro-9-(2-deoxy-β-D-arabinofuranosyl)adenine (corresponding to "cladribine") or a pharmaceutically acceptable salt thereof, and a hepatoma virus is HCV.
(7) A prophylactic or therapeutic agent for a hepatoma virus-related disease, which contains the anti-hepatoma virus agent according to (1), wherein the related disease is selected form the group consisting of chronic hepatitis, liver cirrhosis, and liver cancer.
(8) The prophylactic or therapeutic agent according to (7), which contains 2-chloro-9-(2-deoxy-2-fluoro-β-D-arabinofuranosyl)adenine or a pharmaceutically acceptable salt thereof as the anti-hepatoma virus agent, wherein the hepatoma virus-related disease is a disease related to HBV and/or HCV.
(9) The prophylactic or therapeutic agent according to (7), which contains 2-chloro-9-(2-deoxy-2-fluoro-β-D-arabinofuranosyl)adenine or a pharmaceutically acceptable salt thereof as the anti-hepatoma virus agent, wherein the hepatoma virus-related disease is a disease related to HBV or HCV.
(10) The prophylactic or therapeutic agent according to (7), which contains 2-chloro-9-(2-deoxy-2-fluoro-β-D-arabinofuranosyl)adenine or a pharmaceutically acceptable salt thereof as the anti-hepatoma virus agent, wherein the hepatoma virus-related disease is a disease related to HBV.
(11) The prophylactic or therapeutic agent according to (7), which contains 2-chloro-9-(2-deoxy-2-fluoro-β-D-arabinofuranosyl)adenine or a pharmaceutically acceptable salt thereof as the anti-hepatoma virus agent, wherein the hepatoma virus-related disease is a disease related to HCV.
(12) The prophylactic or therapeutic agent according to (7), which contains 2-chloro-9-(2-deoxy-β-D-arabinofuranosyl) adenine or a pharmaceutically acceptable salt thereof as the anti-hepatoma virus agent, wherein the hepatoma virus-related disease is a disease related to HCV.

The present description includes part or all of the contents as disclosed in the description and/or drawings of Japanese Patent Application No. 2016-048664, which is a priority document of the present application.

Advantageous Effects of Invention

According to the present invention, an antiviral agent targeted to HBV and HCV that are hepatoma viruses and a prophylactic or therapeutic agent for HBV- and HCV-related diseases such as liver cancer can be provided. Further, according to the present invention, an antiviral agent targeted to HCV and a prophylactic or therapeutic agent for HCV-related diseases such as liver cancer can be provided.

DESCRIPTION OF EMBODIMENTS

Figure 1:
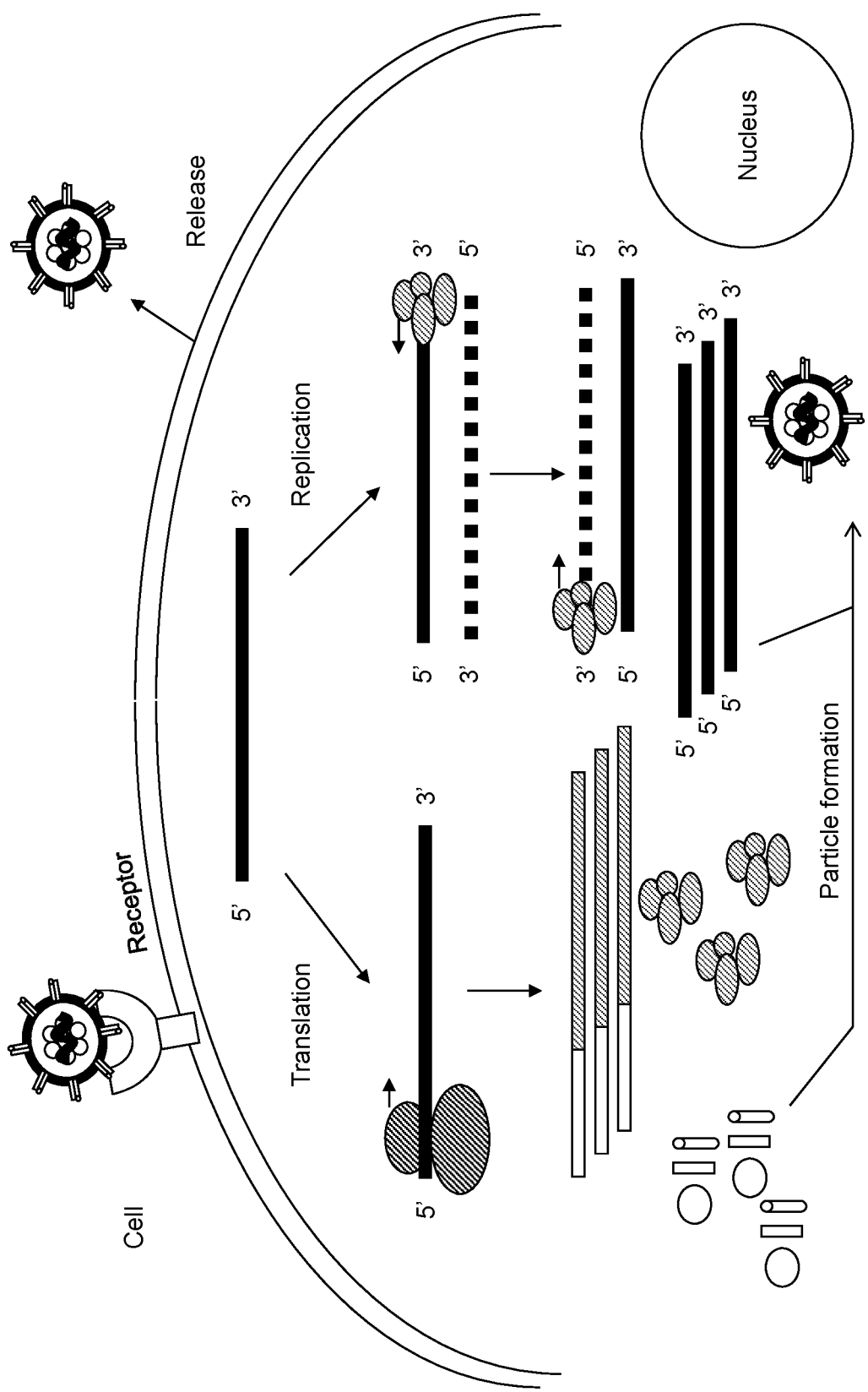
FIG. 1 illustrates the life cycle of HCV.
Figure 2:
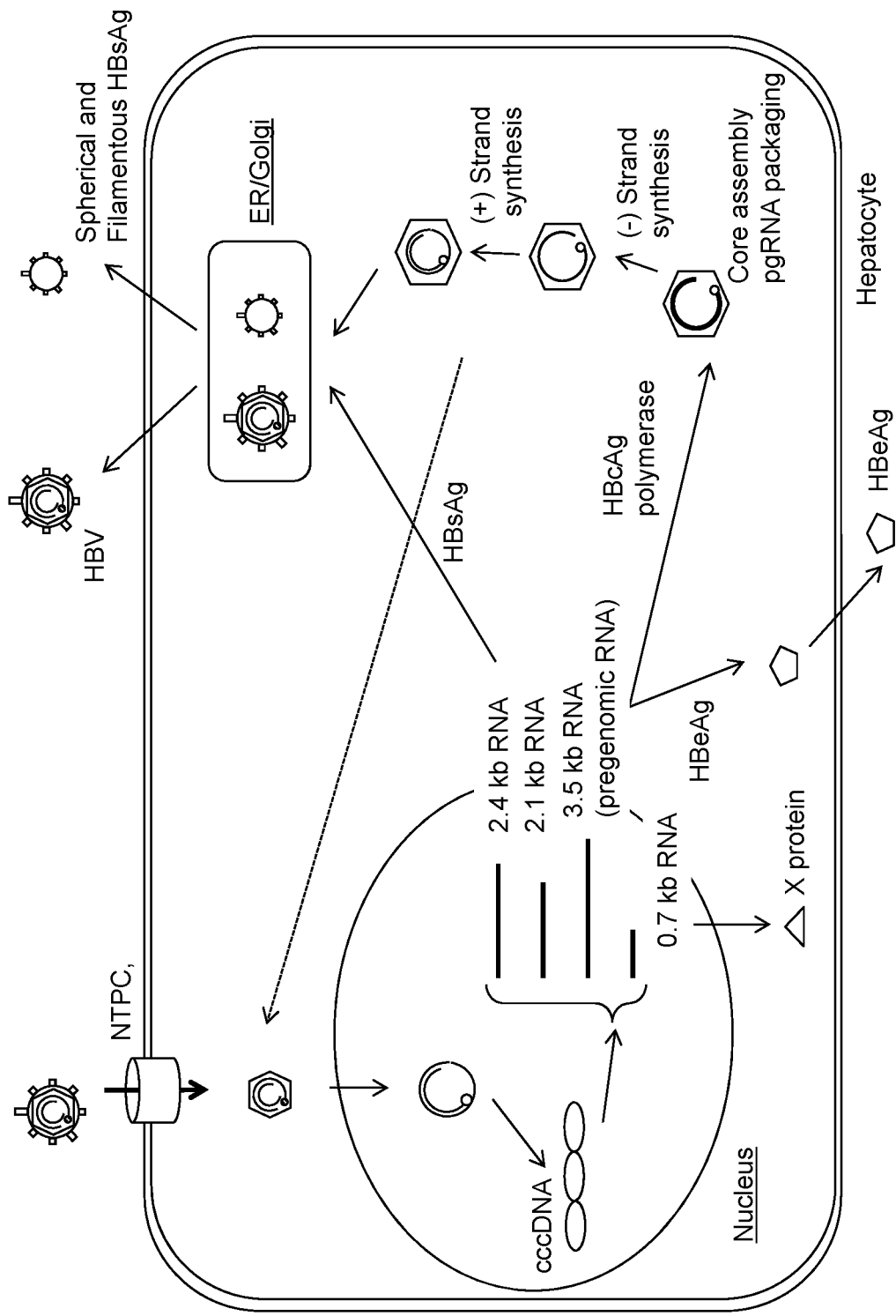
FIG. 2 illustrates the life cycle of HBV.

Hereinafter, the present invention will be described in detail.

The anti-hepatoma virus agent according to the present invention contains as an active ingredient a compound represented by the following Formula (I) or a pharmaceutically acceptable salt thereof:

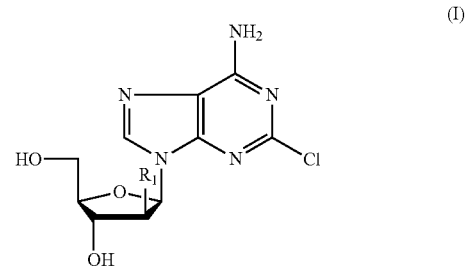

(I)

(wherein $R_1$ is fluorine or hydrogen). Hepatoma virus (HBV and/or HCV) infections can be prevented or treated according to the anti-hepatoma virus agent of the present invention.

Further, according to the anti-hepatoma virus agent of the present invention, by preventing or treating hepatoma viral infections, it is possible to further prevent or treat hepatoma virus-related diseases. Thus, the anti-hepatoma virus agent according to the present invention can also serve as a prophylactic or therapeutic agent for hepatoma virus-related diseases. The term "hepatoma virus-related disease" used herein refers to a disease that is developed due to infection with a hepatoma virus. Examples thereof include chronic hepatitis, liver cirrhosis, and liver cancer.

Furthermore, the present invention relates to a method for preventing or treating a hepatoma virus infection or a method for preventing or treating a hepatoma virus-related disease, comprising administering the above-described compound represented by Formula (I) or a pharmaceutically acceptable salt thereof to a subject (patient) such as a human or an animal.

In a first embodiment of the present invention, an anti-hepatoma virus agent against both HBV and HCV according to the present invention (hereinafter referred to as the "anti-hepatoma virus agent according to the first embodiment of the present invention") contains as an active ingredient 2-chloro-9-(2-deoxy-2-fluoro-β-D-arabinofuranosyl)adenine (provided that $R_1$ is fluorine for the compound represented by Formula (I)), which is also referred to as "clofarabine," or a pharmaceutically acceptable salt thereof.

The chemical structural formula of clofarabine and the chemical structural formulae of cladribine and fludarabine used in the Examples described later are shown below.

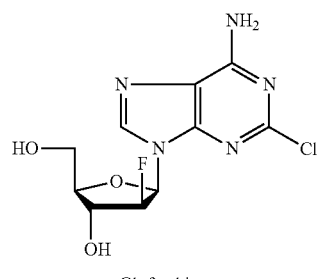

Clofarabine

-continued

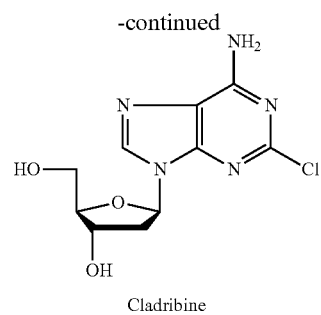

Cladribine

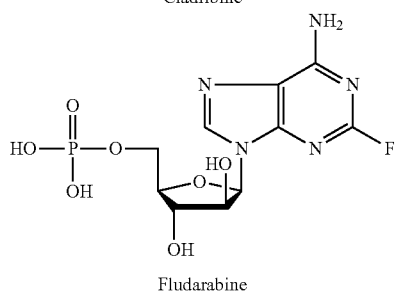

Fludarabine

As shown in the Examples below, the present inventors found that F at position 2 of the ribose of clofarabine is important for anti-HBV activity of clofarabine because cladribine that is formed by substituting F at position 2 of the ribose of clofarabine by H does not have anti-HBV activity. Further, the prevent inventors found that since cladribine has anti-HCV activity but not anti-HBV activity, 2-chloroadenine that is a base common to clofarabine and cladribine is important for anti-HCV activity.

Further, according to the anti-hepatoma virus agent of the first embodiment of the present invention, by preventing or treating both HBV and HCV infections, it is possible to further prevent or treat HBV and/or HCV-related diseases. Thus, the anti-hepatoma virus agent according to the first embodiment of the present invention can also serve as a prophylactic or therapeutic agent for HBV and/or HCV-related diseases. The term "HBV and/or HCV-related disease" used herein refers to a disease that is developed due to infection with HBV and/or HCV. Examples thereof include chronic hepatitis, liver cirrhosis, and liver cancer.

Clofarabine used in the present invention can be produced in accordance with a method described in, for example, Bauta W. E. et al., Organic Process Research & Development 2004, Vol. 8, No. 6, pp. 889-896. In addition, commercially available products thereof such as Clofarabine (C2500) (Tokyo Chemical Industry Co., Ltd.) may be used.

Further, examples of a pharmaceutically acceptable salt of clofarabine include: salts with inorganic acids such as hydrochloric acid, sulfuric acid, phosphoric acid, hydrobromic acid, hydroiodic acid, nitric acid, pyrosulfuric acid, and metaphosphoric acid; salts with organic acids such as citric acid, benzoic acid, acetic acid, propionic acid, fumaric acid, maleic acid, and sulfonic acid (e.g., methanesulfonic acid, p-toluenesulfonic acid, or naphthalenesulfonic acid); and alkali metal salts such as sodium salts and potassium salts.

The anti-hepatoma virus agent according to the first embodiment of the present invention can be administered depending on the dosage form by a variety of known methods, and the dose, dosing site, dosing interval, dosing period, and the like can be appropriately determined in consideration of patient's age, weight, and pathological conditions or the combination use of the agent with other agents or therapies. Examples of the administration method include, but are not particularly limited to, oral administration, injection, and intravenous drip infusion.

The dose of anti-hepatoma virus agent according to the first embodiment of the present invention may vary depending on the dosage form, administration method, or symptoms to be treated. However, for example, the dose per body surface area ($m^2$) can be set to 3 mg to 5.2 mg and preferably 30 to 52 mg in terms of the amount of an active ingredient (clofarabine or a pharmaceutically acceptable salt thereof), and the agent can be administered at an appropriate dosing frequency such as once or several times daily or once per several days or via continuous drip infusion or the like.

Dosage forms of the anti-hepatoma virus agent according to the first embodiment of the present invention include, but are not particularly limited to, infusions, tablets, capsules, powders, granules, suppositories, and injections. In addition, the anti-hepatoma virus agent according to the first embodiment of the present invention may contain, for example, components such as a pharmaceutical carrier, an excipient, and a stabilizer.

The present invention also relates to a method for preventing or treating an HBV and/or HCV infection or a method for preventing or treating an HBV and/or HCV-related disease, comprising administering clofarabine or a pharmaceutically acceptable salt thereof to a subject (patient) such as a human or an animal. The dosage form, dosing mode, dose, and the like of clofarabine or a pharmaceutically acceptable salt thereof can be determined in accordance with the anti-hepatoma virus agent according to the first embodiment of the present invention described above.

Meanwhile, the following points are mentioned as advantageous effects of the present invention.

1) Individuals Infected with HCV and HBV are Subjects

The present application discloses that clofarabine was bound to have anti-HBV activity and anti-HCV activity. Since the conventional anti-HBV agents are not effective for HCV, subjects of the agents are HBV-infected individuals (about 350 million people in the world). In addition, since the conventional anti-HCV agents are not effective for HBV, subjects of the agents are HCV infected individuals (about 200 million people in the world). Meanwhile, since clofarabine is effective against both HCV and HBV, subjects of the agent will be expanded to about 550 million people in total in the world. Drug development requires enormous development cost. However, since clofarabine itself can cover two infections, the development cost can be expected to be reduced. Further, as clofarabine has been currently used for leukemia in clinical practice, the development cost can be expected to be reduced.

2) Reduction of Safety Risk

Clofarabine is an agent that has been currently used for leukemia in clinical practice, and therefore, it is guaranteed in terms of safety evaluation. Furthermore, clofarabine exhibits anti-HBV activity at a concentration one-hundredth (about 20 nM) of the effective blood level (about 2 μM) for leukemia. Therefore, when clofarabine is used for hepatitis, significant reduction of adverse drug reactions can be expected as compared with the use of clofarabine for leukemia.

3) Use of Clofarabine for Other Viruses

Except for physiologically active substances, clofarabine is the first antiviral agent that is effective against DNA viruses and RNA viruses having different life cycles. This suggests that clofarabine is an antiviral agent having a broad spectrum. At present, there are very few antiviral agents developed for viral infections. There are currently no antiviral agents existing for most of viruses. Clofarabine can be expected to be used also against pathogenic viruses for which no antiviral agents exist. Further, since clofarabine is the first discovered mDAA, it is believed to have a potential to be an effective antiviral agent against an outbreak of an unknown virus that would be a threat to mankind. In a situation that a highly pathogenic virus arises and there is no time to develop a novel antiviral agent, it is assumed that the presence of mDAA will be very important for the survival of mankind. Moreover, as mankind is recently exposed to the threat of terrorism, mDAA is considered useful also against bioterror attacks using unknown viruses.

Meanwhile, in a second embodiment of the present invention, an anti-hepatoma virus agent against HCV according to the present invention (hereinafter referred to as the "anti-hepatoma virus agent according to the second embodiment of the present invention") contains as an active ingredient 2-chloro-9-(2-deoxy-β-D-arabinofuranosyl)adenine (provided that $R_1$ is hydrogen for the compound represented by Formula (I)), which is also referred to as "cladribine," or a pharmaceutically acceptable salt thereof.

Further, according to the anti-hepatoma virus agent of the second embodiment of the present invention, by preventing or treating an HCV infection, it is possible to further prevent or treat HCV-related diseases. Thus, the anti-hepatoma virus agent according to the second embodiment of the present invention can also serve as a prophylactic or therapeutic agent for HCV-related diseases. The term "HCV-related disease" used herein refers to a disease that is developed due to infection with HCV. Examples thereof include chronic hepatitis, liver cirrhosis, and liver cancer. Further, the present invention also relates to a method for preventing or treating an HCV infection or a method for preventing or treating an HCV-related disease, comprising administering cladribine or a pharmaceutically acceptable salt thereof to a subject (patient) such as a human or an animal.

Cladribine used in the present invention can be produced in accordance with a method described in, for example, Lioux T. et al., Eur. J. Org. Chem., 2003, Vol. 2003, Issue 20, pp. 3997-4002. In addition, commercially available products thereof such as Cladribine (C2499) (Tokyo Chemical Industry Co., Ltd.) may be used.

Further, examples of a pharmaceutically acceptable salts of cladribine include: salts with inorganic acids such as hydrochloric acid, sulfuric acid, phosphoric acid, hydrobromic acid, hydroiodic acid, nitric acid, pyrosulfuric acid, and metaphosphoric acid; salts with organic acids such as citric acid, benzoic acid, acetic acid, propionic acid, fumaric acid, maleic acid, and sulfonic acid (e.g., methanesulfonic acid, p-toluenesulfonic acid, or naphthalenesulfonic acid); and alkali metal salts such as sodium salts and potassium salts.

The dosage form, dosing mode, dose, and the like of cladribine or a pharmaceutically acceptable salt thereof can be determined in accordance with the dosage form, dosing mode, dose, and the like of clofarabine or a pharmaceutically acceptable salt thereof in the anti-hepatoma virus agent according to the first embodiment of the present invention described above.

EXAMPLES

The present invention will be specifically described with reference to the following Examples. However, these Examples are not intended to limit the scope of the present invention.

Anti-HBV Activity and Anti-HCV Activity of Clofarabine and Anti-HCV Activity of Cladribine 1. Materials and Methods 1-1. Determination of Anti-HBV Activity Anti-HBV activity was evaluated by quantitative PCR for determining the amount of HBV DNA in cells or HBV DNA in the culture supernatant on day 7 after the addition of the agent using the HepG2.2.15 cell line of HBV-producing cells obtained by introducing a gene having a length twice that of the HBV genome into the human liver cancer cell line HepG2. For PCR of HBV DNA, a forward primer (HBV-S190F; 5'-GCT CGT GTT ACA GGC GGG-3': SEQ ID NO: 1) and a reverse primer (HBV-S703R; 5'-GAA CCA CTG AAC AAA TGG CAC TAG TA-3': SEQ ID NO: 2) were used. PCR was performed by carrying out a reaction at 95° C. for 10 sec, 62° C. for 10 sec, and 72° C. for 30 sec for 35 cycles.

1-2. Evaluation of Anti-HCV Activity

Anti-HCV activity was evaluated using OR6 cells from the human liver cancer cell line HuH-7 and ORL8 cells from the human liver cancer cell line Li23. Since the *Renilla* Luciferase gene has been incorporated into the genome of the genotype-1b O strain in OR6 cells and ORL8 cells, it is possible to conveniently and accurately evaluate the level of HCV RNA replication by determining the *Renilla* Luciferase activity. Each agent was added to OR6 cells or ORL8 cells, the cells were recovered on day 3, and the *Renilla* Luciferase activity was determined.

1-3. Determination of Cytotoxicity

OR6 cells were seeded at a concentration of $3 \times 10^3$ cells/well, and HepG2 NTCP-myc cells were seeded at a concentration of $2 \times 10^4$ cells/well. Each agent was added 24 hours later, and OR6 cells were cultured for 3 days and HepG2 NTCP-myc cells were cultured for 7 days. After the culture, 10 µl of Premix WST-1 Cell Proliferation Assay System (TaKaRa) was added and the cells were further cultured at 37° C. for 2 hours. Thereafter, absorbance was determined at 450 nm using a microplate reader.

2. Results and Discussion

For screening of the anti-HBV agent, the HepG2.2.15 line obtained by introducing the HBV gene into HepG2 cells of a human cancer cell line was used (Production of hepatitis B virus particles in HepG2 cells transfected with cloned hepatitis B virus DNA. Sells M A, Chen M L, and Acs G., Proc. Natl. Acad. Sci. USA 84: 1005-1009 (1987)). For screening of the anti-HCV agent, OR6 cells obtained by introducing the HCV gene into HuH-7 cells of the world-standard human liver cancer cell line were used (Efficient replication of a full-length hepatitis C virus genome, strain O, in cell culture, and development of a luciferase reporter system. Ikeda M, Abe K, Dansako H, Nakamura T, Naka K, Kato N., Biochem. Biophys. Res. Commun., 329(4):1350-9 (2005)). In addition to the above, the ORL8 cell line obtained by introducing the HCV gene into cells of the human liver cancer cell line Li23 that has been originally developed by the present inventors were also used (Efficient replication systems for hepatitis C virus using a new human hepatoma cell line. Kato N, Mori K, Abe K, Dansako H, Kuroki M, Ariumi Y, Wakita T, Ikeda M., Virus Res., 146(1-2):41-50 (2009)). Except for the present inventors, screening of anti-HCV agents has been carried out using only the HuH-7 cell line in the world. Since the intracellular environment differs between HuH-7 cells and Li23 cells, by using Li23 cells, it is possible to identify agents that would be overlooked by screening conducted using only HuH-7 cells.

Further, in this Example, in order to realize reduction of the period for developing agents against hepatoma viruses, safety ensuring, and drug price reduction, drug repositioning for reevaluation of drugs that have been approved as pharmaceuticals was conducted.

Figure 3:
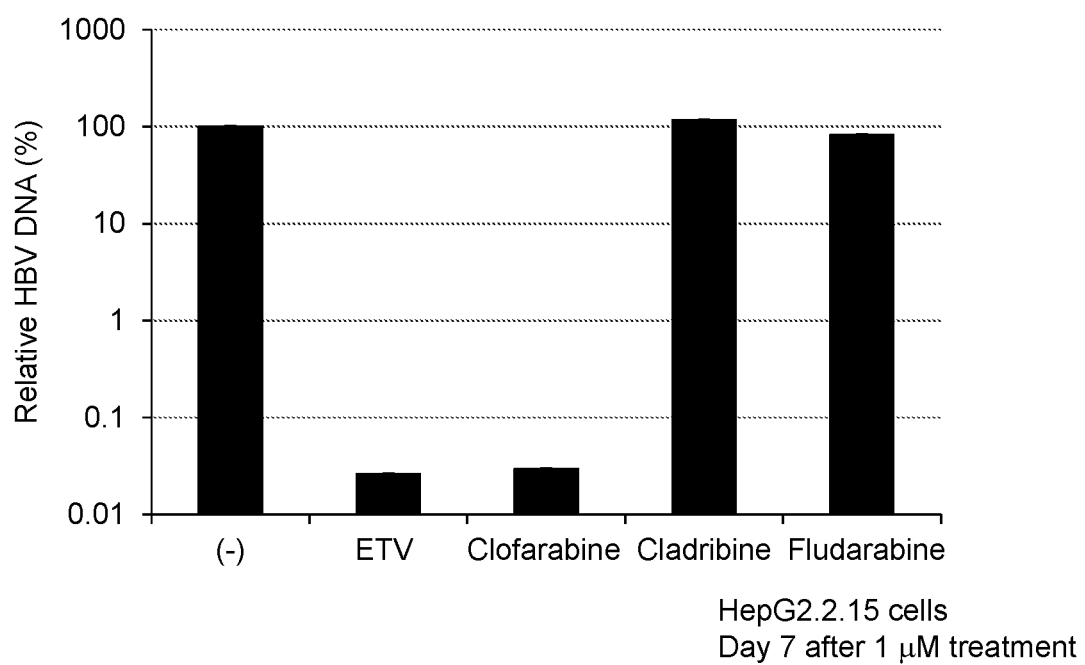
FIG. 3 is a graph showing anti-HBV activity levels of purine antimetabolites. HepG2.2.15 cells were seeded at a concentration of $1 \times 10^5$ cells/well. Then, 24 hours later, purine antimetabolites (clofarabine, cladribine, and fludarabine) and entecavir (ETV) were each diluted to result in a final concentration of 1 μM and each dilution was added to cells. After culture for 7 days, the cytoplasmic fraction was collected and DNA was purified by phenol-chloroform extraction. The intracellular HBV DNA amount was evaluated by quantitative PCR using 20 ng of purified DNA.

In this Example, as shown in FIGS. 3 to 8, screening of anti-HBV activity and screening of anti-HCV activity were carried out simultaneously, thereby identifying clofarabine as an agent capable of suppressing proliferation of both HBV and HCV. Clofarabine showed anti-HBV activity comparable to that of entecavir that is the strongest anti-HBV agent used in clinical practice (FIG. 3). Clofarabine also showed anti-HCV activity comparable to that of sofosbuvir that is the strongest anti-HCV agent used in clinical practice. Except for physiologically active substances such as IFN, clofarabine is the first antiviral agent capable of suppressing proliferation of both HBV and HCV.

It was found that F at position 2 of the ribose of clofarabine is important for anti-HBV activity of clofarabine because cladribine that is formed by substituting F at position 2 of the ribose of clofarabine by H does not have anti-HBV activity (FIG. 3). This indicates that F at position 2 of the ribose is important for the development of nucleic acid analogs having anti-HBV activity.

Figure 4:
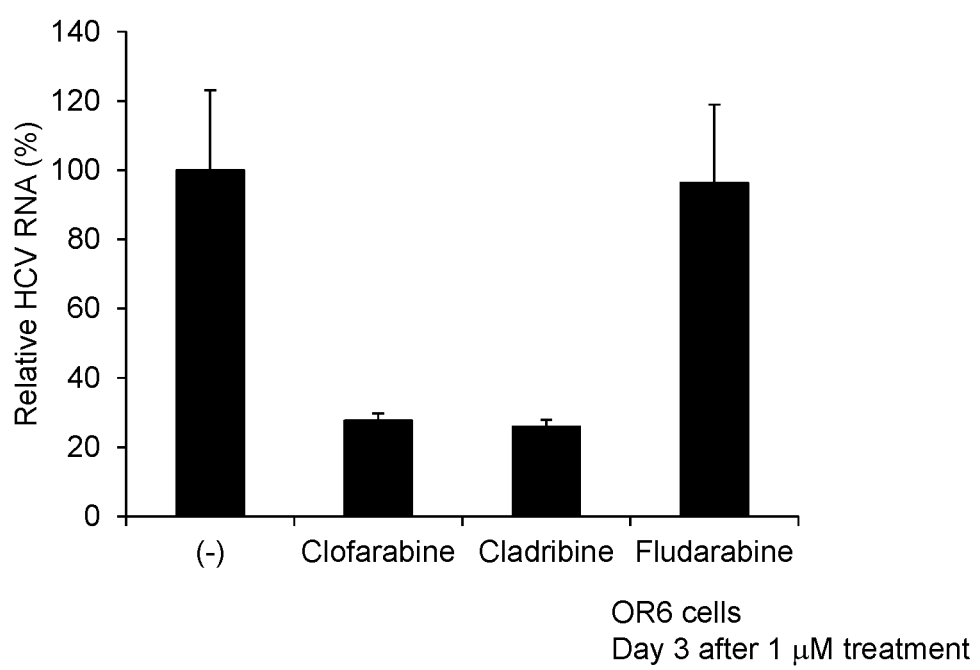
FIG. 4 is a graph showing anti-HCV activity levels of purine antimetabolites. OR6 cells were seeded at a concentration of $1.5 \times 10^4$ cells/well. Then, 24 hours later, purine antimetabolites were each diluted to result in a final concentration of 1 μM and each dilution was added to cells. After culture for 3 days, cells were collected to determine Renilla luciferase activity.
Figure 5:
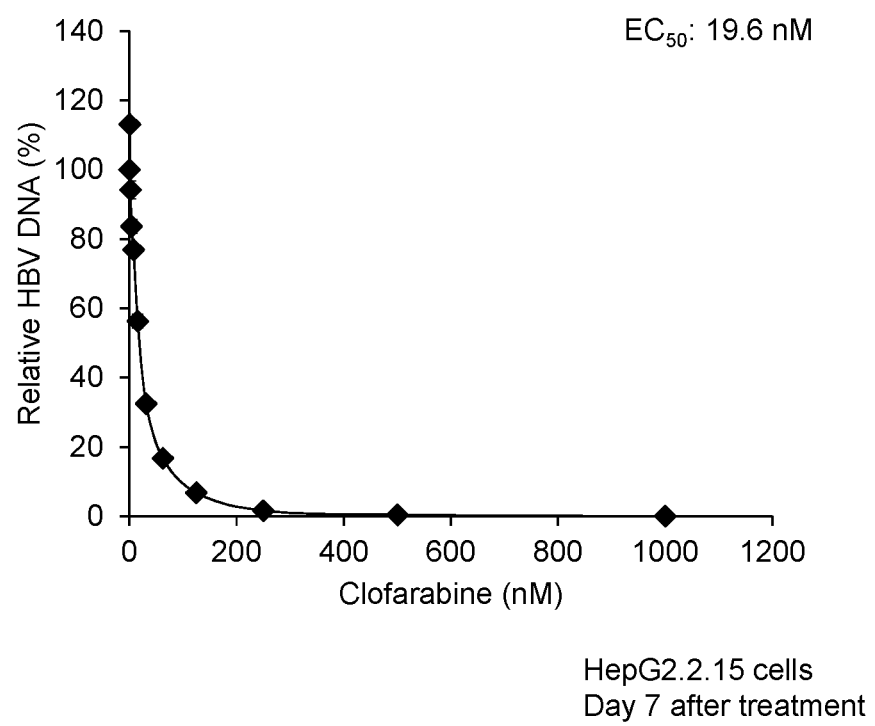
FIG. 5 is a graph showing anti-HBV activity of clofarabine. HepG2.2.15 cells were seeded at a concentration of $1 \times 10^5$ cells/well. Then, 24 hour later, clofarabine was diluted to result in concentrations of 0, 0.97, 1.95, 3.90, 7.81, 15.6, 31.3, 62.5, 125, 250, 500, and 1000 nM and each dilution was added to cells. After culture for 7 days, the cytoplasmic fraction was collected and DNA was purified by phenol-chloroform extraction. The intracellular HBV DNA amount was evaluated by quantitative PCR using 20 ng of purified DNA.
Figure 6:
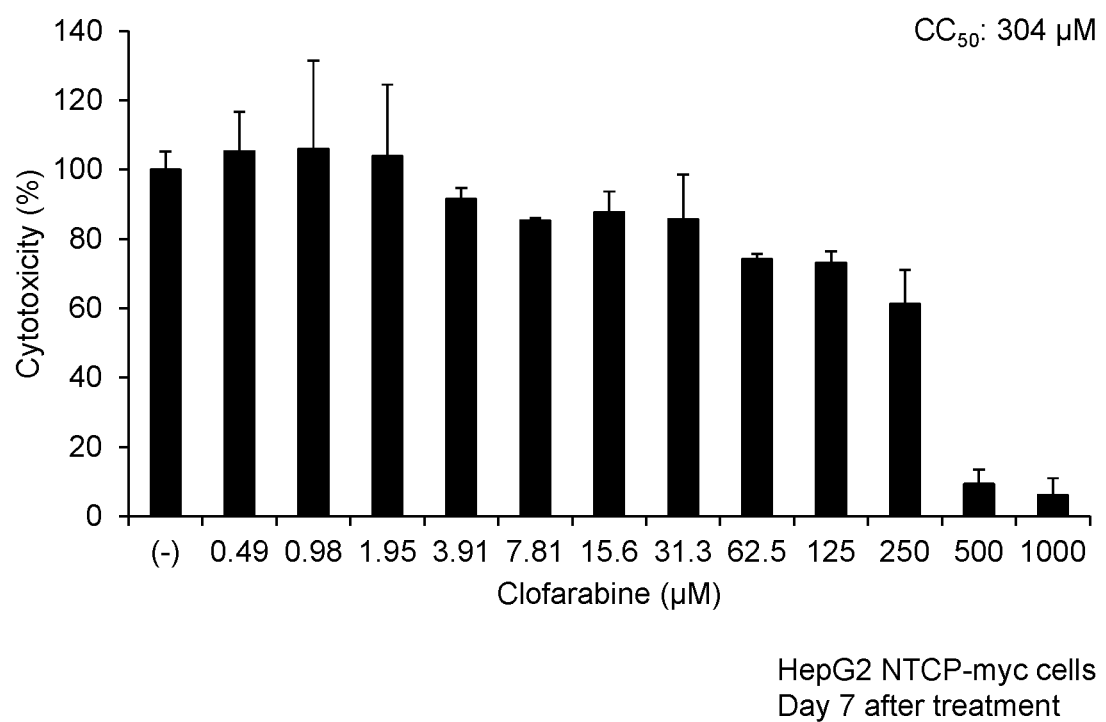
FIG. 6 is a graph showing cytotoxicity (HepG2) of clofarabine. HepG2 NTCP-myc cells were seeded at a concentration of $2 \times 10^4$ cells/well. Then, 24 hour later, clofarabine was diluted to result in concentrations of 0, 0.49, 0.98, 1.95, 3.90, 7.81, 15.6, 31.3, 62.5, 125, 250, 500, and 1000 μM and each dilution was added to cells. After culture for 7 days, 10 μl of Premix WST-1 Cell Proliferation Assay System (TaKaRa) was added and the cells were further cultured at 37° C. for 2 hours. Thereafter, absorbance was determined at 450 nm using a microplate reader.
Figure 7:
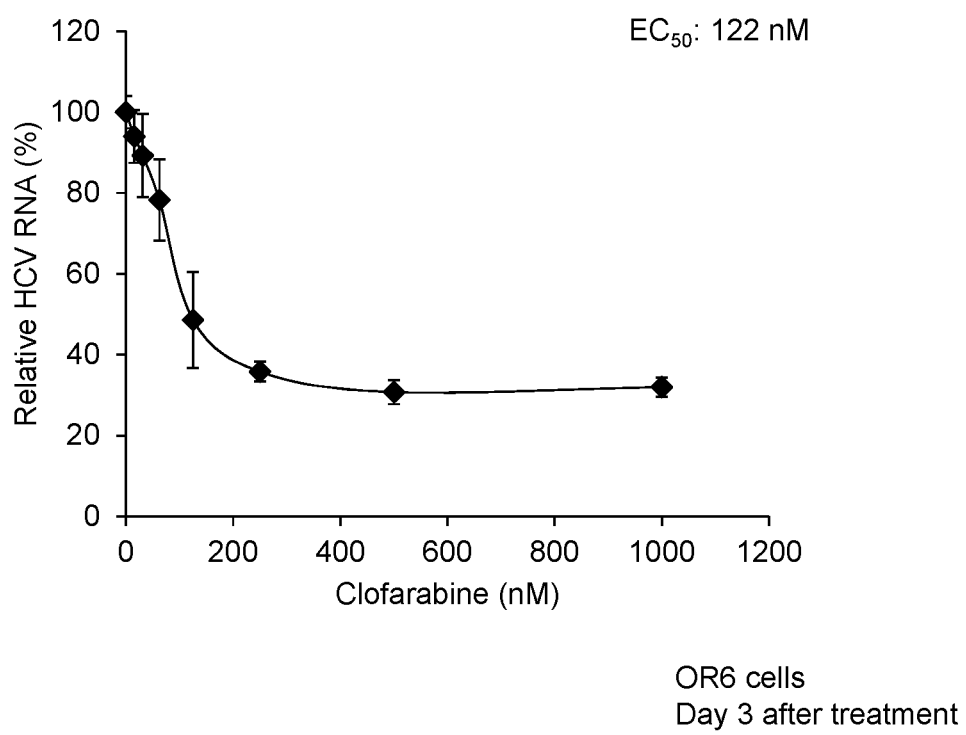
FIG. 7 is a graph showing anti-HCV activity of clofarabine. OR6 cells were seeded at a concentration of $1.5 \times 10^4$ cells/well. Then, 24 hour later, clofarabine was diluted to result in concentrations of 0, 15.6, 31.3, 62.5, 125, 250, 500, and 1000 nM and each dilution was added to cells. After culture for 3 days, cells were collected to determine Renilla luciferase activity.
Figure 8:
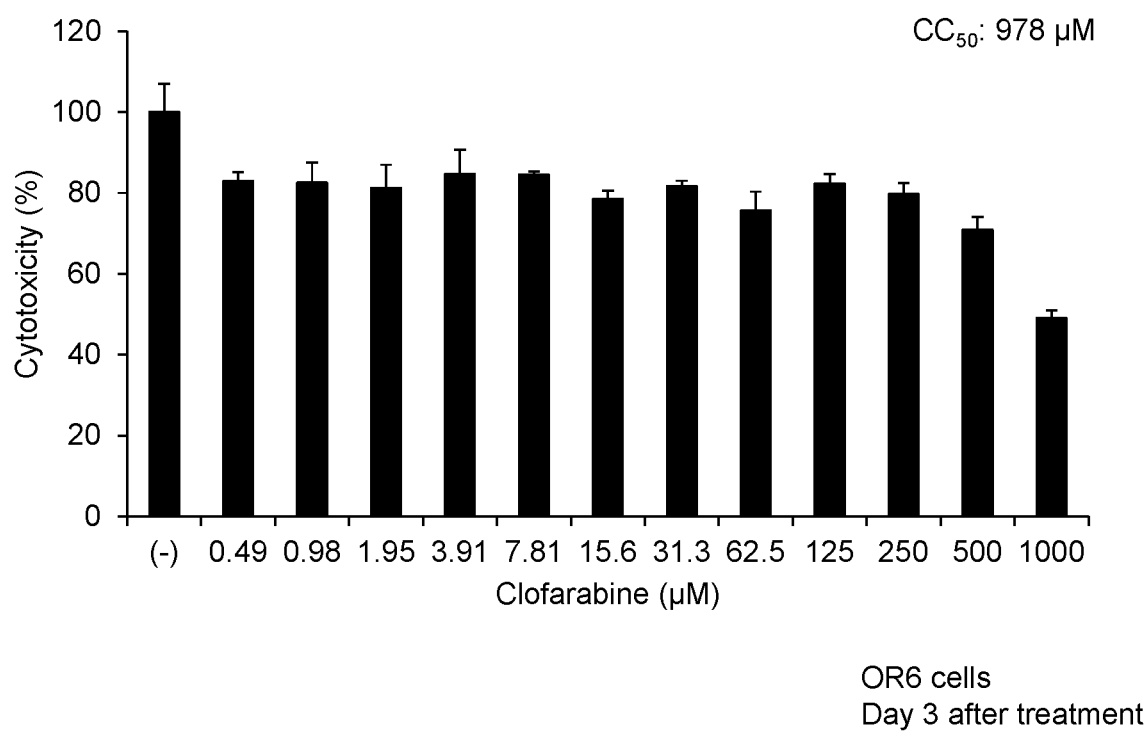
FIG. 8 is a graph showing cytotoxicity (OR6) of clofarabine. OR6 cells were seeded at a concentration of $3 \times 10^3$ cells/well. Then, 24 hour later, clofarabine was diluted to result in concentrations of 0, 15.6, 31.3, 62.5, 125, 250, 500, and 1000 μM and each dilution was added to cells. After culture for 3 days, 10 μl of Premix WST-1 Cell Proliferation Assay System (TaKaRa) was added and the cells were further cultured at 37° C. for 2 hours. Thereafter, absorbance was determined at 450 nm using a microplate reader.

Further, it was found that 2-chloroadenine that is a base common to clofarabine and cladribine is important for anti-HCV activity because cladribine has anti-HCV activity but not anti-HBV activity (FIG. 4). This indicates that it is important that 2-chloroadenine serves as a base for the development of nucleic acid analogs having anti-HCV activity.

Clofarabine is a highly safe pharmaceutical product for refractory leukemia, which was launched by Sanofi in 2013. In the Examples, it was found that clofarabine has a novel effect of exhibiting antiviral activity against HCV and HBV which is totally different from the activity against leukemia. To develop antiviral agents from scratch requires enormous development cost and time. However, in the Examples, the pharmaceutical products, which have been confirmed to be safe, were evaluated by drug repositioning. Therefore, the present invention has highly industrial applicability. One reason that there are ongoing attempts to develop new antiviral agents even though conventional anti-HCV agents and anti-HBV agents are available is that DAA monotherapy against HCV and HBV may result in acquisition of drug-resistant mutations while administration of a plurality of DAAs is unlikely to result in the occurrence of drug-resistant mutations. For the same reason, also in the case of HIV-1, the administration of a plurality of agents in combination but not monotherapy is employed. In this respect, the addition of clofarabine as a new DAA option is beneficial for patients because the risk of failing in treatment due to drug resistance may be reduced.

Since many of anticancer agents have serious drug adverse reactions, there might be hesitation to use clofarabine for chronic hepatitis. However, it would be possible to reduce adverse drug reactions because when clofarabine is used as an antiviral agent for HBV, it exhibits anti-HBV activity at a concentration about one-hundredth of the effective concentration for treatment of leukemia (FIGS. 5 to 8). In addition, the fact that clofarabine is an anticancer agent might be advantageous from different perspectives. In other words, the final purpose of anti-HBV agents and anti-HCV agents is not to simply eliminate the viruses but to prevent liver carcinogenesis by eliminating or suppressing the viruses to inhibit inflammation that causes damage on DNA. At present, it is highly concerned that liver cancer may be developed even after the elimination of HCV in the case of chronic hepatitis C. Clofarabine that is an anticancer agent can be expected to prevent liver carcinogenesis by eliminating not only viruses but also the cause of liver cancer.

Further, since clofarabine has a broad spectrum effective for both DNA viruses and RNA viruses, the applied use of clofarabine against viruses for which no therapeutic agents are currently available or preparation of clofarabine for a potential outbreak of an unknown virus can be expected.

All publications, patents and patent applications cited in the present description are incorporated herein by reference in their entirety.

The invention claimed is:

1. A method for treating a hepatoma virus infection, comprising administering an effective amount of a compound Formula (I)

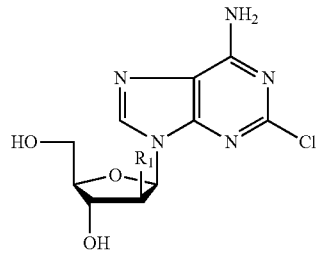

wherein $R_1$ is fluorine
or a pharmaceutically acceptable salt thereof to a patient in need thereof; and
wherein the hepatoma virus is hepatitis B virus and/or hepatitis C virus.

2. The method of claim 1, wherein the patient is a human.

3. The method of claim 1, wherein the hepatoma virus is hepatitis B virus or hepatitis C virus.

4. The method of claim 1, wherein the hepatoma virus is hepatitis B virus.

5. The method of claim 1, wherein the hepatoma virus is hepatitis C virus.

6. A method for treating a hepatoma virus-related disease, comprising administering an effective amount of a compound Formula (I)

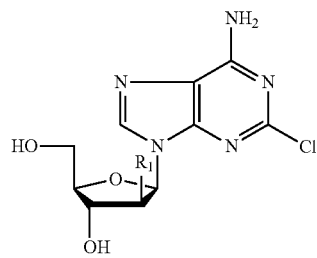

wherein $R_1$ is fluorine
or a pharmaceutically acceptable salt thereof to a patient in need thereof,
wherein the related disease is chronic hepatitis; and
wherein chronic hepatitis related to hepatitis B virus and/or hepatitis C virus.

7. The method of claim 6, wherein the patient is a human.

8. The method of claim 6, wherein the related disease is a disease related to hepatitis B virus or hepatitis C virus.

9. The method of claim 6, wherein the related disease is a disease related to hepatitis B virus.

10. The method of claim 6, wherein the related disease is a disease related to hepatitis C virus.

* * * * *